US011237622B2

(12) United States Patent
Modre-Osprian et al.

(10) Patent No.: US 11,237,622 B2
(45) Date of Patent: Feb. 1, 2022

(54) METHOD FOR DETERMINING THE TIME REQUIRED FOR A TIMED UP AND GO TEST

(71) Applicant: AIT AUSTRIAN INSTITUTE OF TECHNOLOGY GMBH, Vienna (AT)

(72) Inventors: Robert Modre-Osprian, Ligist (AT); Peter Kastner, Seiersberg-Pirker (AT); Guenter Schreier, Graz (AT); Alberto Sanchez Sanchez, Getafe (ES)

(73) Assignee: AIT Austrian Institute of Technology GmbH, Vienna (AT)

( * ) Notice: Subject to any disclaimer, the term of this patent is extended or adjusted under 35 U.S.C. 154(b) by 350 days.

(21) Appl. No.: 16/313,946

(22) PCT Filed: May 31, 2017

(86) PCT No.: PCT/AT2017/060140
§ 371 (c)(1),
(2) Date: Dec. 28, 2018

(87) PCT Pub. No.: WO2018/000007
PCT Pub. Date: Jan. 4, 2018

(65) Prior Publication Data
US 2019/0155377 A1 May 23, 2019

(30) Foreign Application Priority Data
Jun. 30, 2016 (AT) .............................. A 50590/2016

(51) Int. Cl.
G06F 3/01 (2006.01)
A61B 5/00 (2006.01)
(Continued)

(52) U.S. Cl.
CPC ............ *G06F 3/011* (2013.01); *A61B 5/1126* (2013.01); *A61B 5/6891* (2013.01);
(Continued)

(58) Field of Classification Search
CPC ....... G06F 3/011; G06F 3/017; G01B 11/026; G01B 17/00; A61B 5/1126; A61B 5/6891
See application file for complete search history.

(56) References Cited

U.S. PATENT DOCUMENTS

| 10,568,547 | B1* | 2/2020 | Johanning | A61B 5/225 |
| 2015/0272511 | A1* | 10/2015 | Najafi | A61B 5/7275 600/301 |
| 2017/0154514 | A1* | 6/2017 | Condon | G08B 21/182 |

FOREIGN PATENT DOCUMENTS

JP 2015216953 A 12/2015

OTHER PUBLICATIONS

NPL search using keywords: "Timed Up Go" chair walk duration distance threshold, Mar. 24, 2021, 4pp. (2016).*

(Continued)

Primary Examiner — Toan M Le
Assistant Examiner — Xiuqin Sun
(74) Attorney, Agent, or Firm — Laurence A. Greenberg; Werner H. Stemer; Ralph E. Locher

(57) ABSTRACT

A method determines the time required for a timed up and go test and for verifying an ascertained result. A distance measuring device is provided which continuously measures the distance from a subject located in front of a chair to the backrest of the chair and which forwards the distance to a control unit. The chair is positioned in particular at a specified distance to a wall, an obstacle, or a marking. The measured distance values recorded by the distance measuring device are continuously recorded. The subject is instructed to stand up from the chair, walk forwards, in particular towards the wall, the obstacle, or the marking, and then turn around, in particular in front of the wall, the obstacle, or in the region of the marking, and sit back down on the chair. The subject carries out these instructions to the best of their ability.

21 Claims, 2 Drawing Sheets

(51) Int. Cl.
*A61B 5/11* (2006.01)
*G01B 11/02* (2006.01)
*G01B 17/00* (2006.01)

(52) U.S. Cl.
CPC ............ *G01B 11/026* (2013.01); *G01B 17/00* (2013.01); *G06F 3/017* (2013.01)

(56) References Cited

OTHER PUBLICATIONS

Goncalves, Jose, et al., Fully-Automated Strength, Agility and Endurance Tests Assessment: An Integrated Low Cost Approach Based on an Instrumented Chair, 2014, p. 6 pp.

Frenken, Thomas, et al., aTUG: Fully-automated Timed Up and Go Assessment Using Ambient Sensor Technologies, 2011, pp. 55-62.

* cited by examiner

METHOD FOR DETERMINING THE TIME REQUIRED FOR A TIMED UP AND GO TEST

BACKGROUND OF THE INVENTION

Field of the Invention

The invention relates to a method for determining the time required for a person to perform a Timed Up and Go Test. The invention further relates to an apparatus with which a Timed Up and Go Test may be performed.

A Timed Up and Go Test is a test in which a subject sits in a chair. In one possible embodiment, the chair is set up at a predetermined distance of preferably three meters from a wall or other obstacle. Alternatively, the chair may also be placed at such a distance from an obstacle or floor marking to indicate to the subject which positioner he should later turn around. Finally, there is also the possibility of leaving the position of the turn-around point completely up to the subject.

The subject is instructed to get up from the chair, go to the wall, turn around in the area of the wall, obstacle, or marking or at a certain distance from the chair, return to the chair and sit down on the chair again. The measured time taken for performing this task is recorded. The time the subject requires in order to perform the task provides insight into the subject's motor skills.

SUMMARY OF THE INVENTION

From the prior art are known both the Timed Up and Go Test, and various possible mechanical aids for carrying out the Timed Up and Go Test. In all methods known in the prior art, means are used that specify the subject's position with respect to the test setup. However, carrying out the test with automated setups is relatively error-prone, so that at the moment it is not possible to achieve a setup that it may be straightforwardly prepared and configured. The objective of the invention is to solve the problems recited above and to make available a method for carrying out a Timed Up and Go Test that is simple to perform, and is virtually independent of the specific conditions of the available space.

The invention accomplishes this task by means of a method according to the independent method claim 1 for determining the time required for a Timed Up and Go Test.

In this method, to determine the time required for a Timed Up and Go Test and verify the result obtained, it is provided that:
 distance measurement equipment is furnished that continuously measures the distance from a subject in front of a chair to the backrest of the chair and forwards said distance to a control unit,
 the chair is positioned in particular at a specified distance from a wall, obstacle, or marking,
 the distance measurements (d) recorded by the distance measurement equipment are continuously recorded,
 the subject is instructed to stand up from the chair, walk forward, in particular toward the wall, obstacle or marking, and then turn around, in particular in front of the wall or the obstacle, or in the region of the marking, and sit back down on the chair, and the subject carries out these instructions to the best of the subject's ability,
 it is checked whether the subject is sitting on the chair, and if the subject has done so for a predetermined time interval, timekeeping is started and a specified start signal is output,
 the timekeeping is stopped when the subject sits back down on the chair,
 a signal (d(t)) is generated from the distance measurements received over the period of time, and the signal is analyzed, in particular after timekeeping has ended, in order to determine
 a) whether the signal (d(t)) continuously increases in a first time range and optionally also whether the signal remains unchanged within the range of measurement error for individual periods of time and
 b) whether the signal continuously decreases again after a specified turn-around threshold value ($d_{th,u}$) is exceeded and optionally also whether the signal remains unchanged within the range of measurement error for individual periods of time until the signal falls below the lower threshold value ($d_{th,s}$), and as long as conditions a) and b) are met, the test is considered to have been completed correctly and the duration of the timekeeping that was required in order to complete the test is kept available and is optionally displayed.

With this method it is straightforwardly possible to establish whether the Timed Up and Go Test has been performed correctly and to readily obtain the time required for doing so. In particular, this test may be performed by the subject on their own, without the assistance of an additional person.

A particularly preferred implementation of the test allows an automatic start and provides that the distance measurements obtained are continuously examined before carrying out the test, and if the distance measurements fail to reach a lower threshold value for a predetermined period of time, in particular if the subject is sitting down, the start signal is emitted, causing timekeeping to commence and signaling to the subject that the test is starting.

In order for an additional person to be able to carry out the test independently of the subject, it may be provided that an external trigger signal causes the emission of the start signal and the start of timekeeping.

Alternatively, to this end, it may be provided that the timekeeping is started when a sensor located in the seat surface of the chair, in particular a pressure sensor, detects a drop in pressure below a predetermined threshold value.

For the automatic termination of a test, it may be provided that, if the distance measurements fall below a lower threshold value after exceeding an additional threshold value for a predetermined period of time, in particular if the subject (1) is again sitting on the chair (FIG. 4), the test has been completed and timekeeping is stopped.

For the test to be completed by one person, it may be provided that an external trigger signal terminates the timekeeping, or that the timekeeping is terminated when a sensor placed in the seat surface of the chair, in particular a pressure sensor, detects a pressure that exceeds a threshold value.

A simple verification or falsification of the test result provides that that the test is considered to be incorrect, if the increase of the signal (d(t)) exceeds a predetermined increase threshold, and/or if the signal (d(t)) has readings corresponding to the distance of the chair (5) from the wall (2) or obstacle or has measurements that exceed the distance from the chair to the marking by a predetermined threshold value, and/or if none of the distance measurements (d) of the signal (d(t)) reaches a predetermined threshold value ($d_{th,u}$) and the subject does not reach the turn-around area (32), and/or if timekeeping reaches a maximum time without the test having terminated.

With regard to checking whether the distance measurement equipment is correctly oriented relative to the wall throughout the whole course of measurement, it is provided that the orientation of the distance measurement equipment with respect to the wall or obstacle is continuously monitored, and an error message is issued and the measurement result is invalidated if there are changes in the orientation of the distance measurement equipment or deviations in the orientation of the distance measurement equipment exceeding a threshold value from a predetermined orientation that is in particular horizontal and/or normal to the wall or obstacle.

In straightforwardly creating a recording setup, it is provided that prior to carrying out the test, the distance measurement equipment is arranged on the backrest of the chair and is oriented from the back toward the seated subject.

In addition, for initializing or creating the starting arrangement of the measurement setup, it may be provided that the distance measurements obtained before the start of the test are compared with a predetermined threshold value in such a way as to determine a correct position of the chair, if the distance measurements obtained are within a predetermined distance range and/or if the orientation of the distance measurement equipment corresponds to a predetermined orientation, in particular horizontal and/or normal to the wall or obstacle.

As regards the correct positioning of the chair relative to the wall, it may preferably be provided that the subject is instructed to get up after the test has terminated and go behind the chair or leave the recording area of the distance measurement equipment, and that the correct position and/or orientation of the chair is then checked again according to predetermined criteria, and the test is considered incorrect if the position and/or orientation of the chair to the wall does not meet these criteria.

In a preferred distance measurement, it is provided that the distance measurement equipment determines the distance by means of ultrasonic or laser measurement. By this means, the reliability of the measurement method may be further increased.

A marking, wall or obstacle may be dispensed with in particular if, in particular, a turn-around signal, particularly an acoustic signal, is emitted to induce the subject to turn around when the distance measurements taken by the distance measurement equipment exceed a predetermined distance, in particular when the subject is in the turn-around area.

A preferred embodiment of the invention is illustrated in greater detail with reference to the following drawings.

DESCRIPTION OF THE INVENTION

Figure 1:
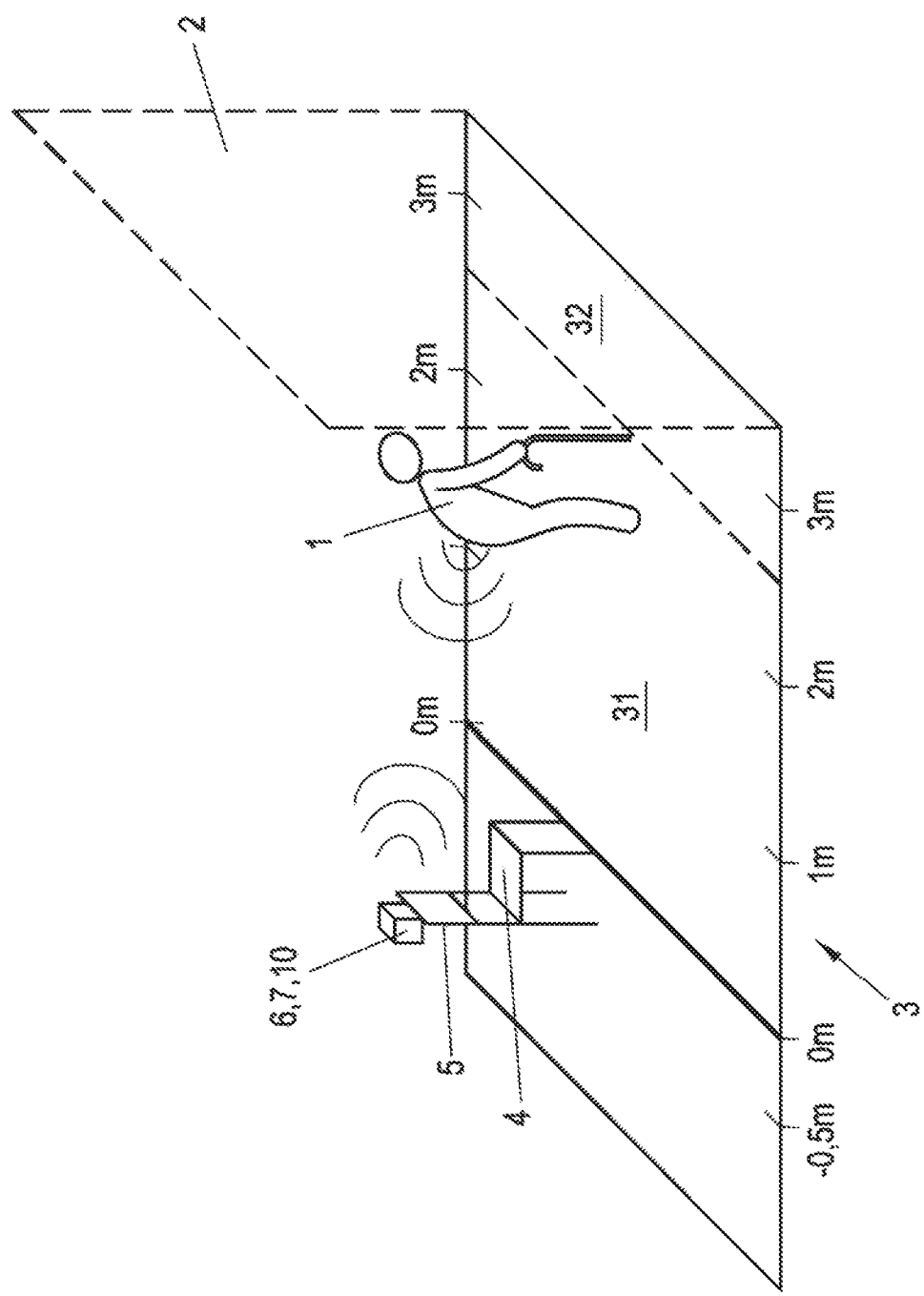
FIG. 1 shows a simple arrangement for performing a Timed Up and Go test.
Figure 2:
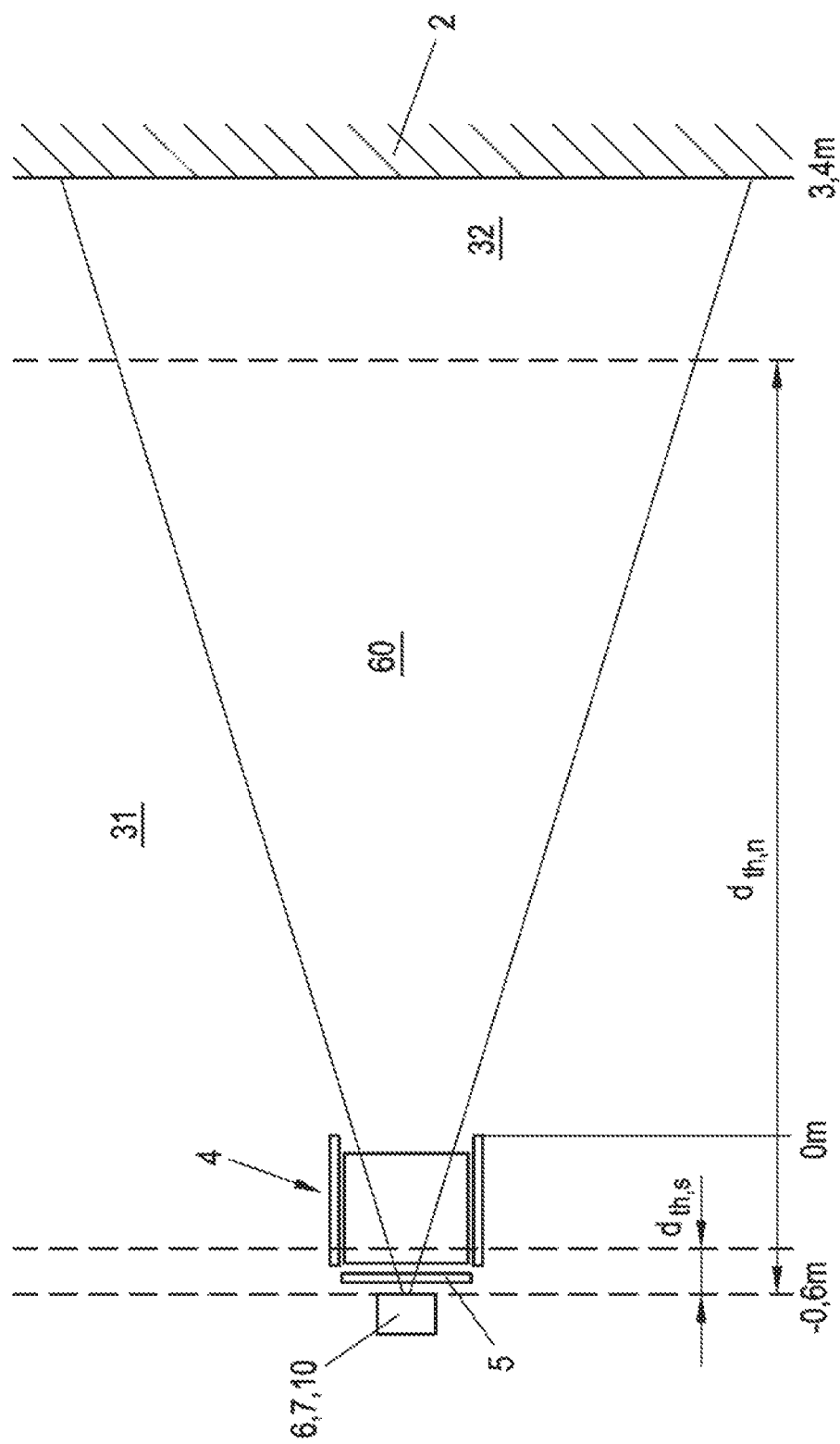
FIG. 2 shows a schematic top view of the arrangement illustrated in FIG. 1.

To prepare for the test, the subject 1 is brought into a test area (FIG. 1) in which are present a wall 2 and a substantially level floor area in front of the wall 2 a substantially level floor area 3. Further present in the area is an apparatus comprising a chair 4 with a backrest 5. On the backrest 5, before executing the test, distance measurement equipment 6 is arranged that is arranged on the back 5 of the chair 4 and is oriented from the backrest 5 toward a subject 1 sitting on the chair. In one embodiment, the distance measurement equipment may be securely connected to the chair 4 or integrated into the chair 4, particularly into the backrest 5 of the chair. In such a case, the specific orientation of the distance measurement equipment relative to the chair 4 may be omitted. The below-mentioned orientation measurement equipment 7 and control unit 10 may also be securely connected to the chair 4, and in particular may be integrated into the chair 4 or into the backrest 5 of the chair 4.

In this case, the chair 4 is oriented in such a way that a subject 1 sitting on the chair 4 in a normal posture will be seated frontally facing the wall 2. The distance measurement equipment 6 is ultrasonic or laser distance measurement equipment; in the arrangement shown in FIG. 1, it determines the distance of the chair back 5 from the wall 2.

In principle, it is not necessary that a solid concrete or wooden wall be present in the test area. It is also of course possible that the wall 2 used for the test is a cabinet or a mobile partition or screen. It is only necessary that the distance measurement equipment 6 identifies the wall 2 when there are no objects or persons other than the subject 1 in the area between the distance measurement equipment 6 and the wall 2.

Instead of a wall 2, another obstacle may also be used that the distance measurement equipment 6 is able to detect. In principle, however, it is not necessary to use a wall 2 or an obstacle for carrying out the test. Instead, it is sufficient if only a marking is visible on the floor, to which the subject orients in order to turn around.

In well-oriented subjects such a marking may also be dispensed with. A marking or wall may also be dispensed with if the subject 1 is given a turn-around signal. This may be determined either by an external person accompanying the test, or on the basis of distance measurements taken by the distance measurement equipment, if these measurements exceed a predetermined threshold value.

If the subject 1 is not in the measurement area of the distance measurement equipment 6, the distance measurement equipment 6 indicates its distance from the wall. For this purpose, the distance measurement equipment 6 is oriented horizontally and normal to the wall 2. Optionally, orientation measurement equipment 7 may be furnished that determines whether the distance measurement equipment 6 is oriented horizontally.

In addition, it may also be determined whether the distance measurement equipment 6 is oriented normal to the wall 2. The distance measurement equipment 6, and optionally the orientation measurement equipment 7, are connected to a control unit 10 that is downstream of the distance measurement equipment 6 and to which the individual distance measurements d of the distance measurement equipment 6 are sent.

During the initialization phase, in addition to the correct orientation of the distance measurement equipment 6, the control unit 10 additionally checks the distance measurements d, i.e. the distance of the backrest 5 from the wall 2, and checks whether the distance measurements d determined in such a way are within a predetermined distance range, which in the present case is about 3.5 meters. If the control unit 10 determines that the distance of the backrest 5 of the chair 4 from the wall 2 is too great or too small relative to the distance range required for the test, this determination is indicated on a display unit located on the control unit 10.

However, the invention is not limited to the exemplary dimensions proposed herein. Thus, it is readily possible to extend the distance for the subject to travel or to expand the turn-around area. The latter is advantageous, for example, if the subject cannot walk without aids and the walking aid such as a walker requires a larger turn-around area, for example, of one meter.

For subjects who are able to walk without aids, a turn-around area with a length of about 40 to 50 cm may be chosen.

After the measuring arrangement has been initialized, the subject 1 sits down on the chair 4. The measured distance of the subject 1 is then measured continuously. If the measured distance measurements d do not reach a predetermined start threshold $d_{th,s}$—if the subject 1 sits on the chair 4, the distance measurements d correspond to a distance of less than 10 cm, so that the start threshold may be set to 10 cm—for a predetermined period of time, for example 5 seconds, the subject 1 is assumed to be sitting on the chair 4. The control unit 10 emits a start signal that signals to the subject 1 that the test is starting. In addition, timekeeping is triggered or started. Alternatively, it is also possible for the timekeeping to be started by a person accompanying the test, who also signals to the subject 1 that the test is starting.

Before the test is carried out, the subject 1 has been instructed to get up from the chair 4, go to the wall 2, turn around in a turn-around area 32 in front of the wall 2, and sit down on the chair 4 again. Distance measurements d are captured continuously during the test and are evaluated over time, and a signal d(t) is created that indicates the distance measurements d captured over the time t. The timekeeping is stopped when the subject 1 sits back down on the chair 4. This may occur via the timekeeping being stopped if the distance measurements fall below a lower threshold value, for example the start threshold, after first exceeding a turn-around threshold value $d_{th,u}$ of e.g. three meters for a predetermined period of time. This is particularly the case when the subject 1 sits back down on the chair 4. The test is terminated and timekeeping is stopped.

Alternatively, the test may also be terminated by a person monitoring the test who sends out a trigger signal that terminates the timekeeping. In addition, the trigger signal may also be generated by another sensor, for example by a pressure sensor integrated into the seat surface of the chair 4, if the measured pressure exceeds a predetermined threshold value.

Subsequently, the signal d(t), consisting of the distance measurements d over time t that were recorded during the test, is analyzed. It is examined whether the generated signal d(t) in a first time range increases continuously in a first time range, and optionally also remains unchanged within the range of measurement error for individual periods, and whether the signal d(t) continuously decreases again after exceeding a predetermined turn-around threshold ($d_{th,u}$) that is somewhat less than the distance from the backrest 5 to the wall 2, and is typically around three meters in a Timed Up and Go test. In this way, it may be determined whether the subject has entered the turn-around area 32. After the subject leaves the turn-around area 32, the signal d(t) should decrease continuously. In this case also, it may be tolerated for the signal value for individual periods to remain unchanged within the range of measurement error, as long as the signal d(t) ultimately falls below the lower threshold value, which corresponds to a distance of about 10 cm from the chair back 5. In this case, the test is considered to be have been completed correctly. The duration of the timekeeping required for this purpose is kept available and optionally displayed. Such measurement errors arise from imprecision of the measurement equipment and also from the movements of the subject that are necessarily associated with walking or standing. For example, a threshold value of 10 to 20 cm may be assumed to be a tolerable measurement error.

For further validation or invalidation of the test, individual signal parameters may be examined in detail. If the rate of increase of the signal d(t) exceeds a predetermined increase threshold, it may be assumed that the subject has moved out of the recording area 60 of the distance measurement equipment 6, causing an abrupt rise in the distance measurement 6. In general, the increase threshold of the signal d(t) may be set at the highest speed that would be expected from the subject 1, optionally increased by a tolerance range. For the present example, the increase threshold may be defined as about 5 m/s.

If distance measurements d are captured in the signal that correspond to the distance from the chair 4 or the backrest 5 of the chair 4 to the wall 2, it may be assumed that the subject 1 is not in the recording area 60 of the distance measurement equipment 6, because otherwise, if the subject 1 had been detected in the recording area 60 between the distance measurement equipment 6 and the wall 2, the distance measurement d would be lower. For this reason, a test may be invalidated or rejected as incorrect if there are distance measurements d in the signal d(t) that correspond to the distance from the backrest 5 of the chair 4 to the wall 2.

Another criterion for invalidating a signal d(t) captured in the course of the test consists of examining the signal d(t) for whether the subject 1 has actually reached a turn-around area 32 in front of the wall 2, i.e. whether the subject has reached a minimum distance $d_{th,u}$ from the chair back 5, which is about three meters in the exemplary embodiment of the Timed Up and Go test. If the distance measurements d of the signal d(t) do not reach the turn-around area 32 or the minimum distance $d_{th,u}$, and the test is terminated in advance, the test may be considered incorrect and the result rejected, on the assumption that the subject 1 did not reach the wall 2 during the test.

In addition, the test may be stopped even if the timekeeping reaches a maximum time without the test having terminated. In some cases, the subject may not to return to chair 4 due to falling or mental confusion.

In addition, it is also possible, throughout the test, to continuously monitor whether the orientation of the distance measurement equipment 6 corresponds to the originally set orientation or whether changes in the orientation of the distance measurement equipment 6 have led to a distortion of the Timed Up and Go test. In the case of changes in the orientation of the distance measurement equipment 6 or deviations in the orientation of the distance measurement equipment 6 by more than a threshold value from a predetermined orientation that is in particular horizontal and/or normal to the wall, an error message is output and the measurement result is invalidated.

Another check at the end of the test may further improve the test's validity. For this purpose, the subject 1 is instructed to stand up after the test has terminated and go behind the chair 4 or leave the recording area of the distance measurement equipment 6. Subsequently, the criteria mentioned above, for assessing the correct position and/or orientation of the chair 4 to the wall 2 or to the obstacle, are checked again.

In this context, for example, the orientation of the chair to the wall 2 may be checked again: Deviations of the orientation of the distance measurement equipment 6 from a predetermined orientation that is in particular horizontal and/or normal to the wall 2 or obstacle, render the measurement result invalid.

Likewise, the determined distance measurements may also be compared with a predefined threshold value after the test has completed, and, in this way, it may be determined that a position of the chair was correct if the distance measurement obtained is within a predetermined distance range. If this is not the case, the test is considered incorrect.

The invention claimed is:

1. A method for determining a time required for a Timed Up and Go Test and verifying a result obtained, the method comprises the steps of:
   furnishing distance measurement equipment that continuously measures a distance from a subject in front of a chair to a backrest of the chair and forwards the distance to a controller during a test;
   positioning the chair at a specified distance from a wall, obstacle, or marking;
   continuously recording distance measurements by the distance measurement equipment;
   comparing the distance measurements obtained before a start of the test with a predetermined threshold value and in this way, a correct position of the chair is determined, if the distance measurements obtained are within a predetermined distance range and/or if the orientation of the distance measurement equipment corresponds to a predetermined orientation;
   instructing the subject to stand up from the chair, walk forward toward the wall, the obstacle or the marking, and then turn around, and sit back down on the chair, and the subject carries out instructions to a best of an ability of the subject;
   checking whether the subject is sitting on the chair and if the subject has done so for a specified time interval, timekeeping is started and a specified start signal is output;
   stopping the timekeeping when the subject sits back down on the chair;
   generating a signal from the distance measurements received over a period of time, and the signal is analyzed in order to determine:
      a) whether the signal continuously increases in a first time range and; and
      b) whether the signal continuously decreases again after a predetermined turn-around threshold value is exceeded and; and
   assuming, as long as the conditions a) and b) are met, the test is considered to have been completed correctly and a duration of the timekeeping that was required in order to complete the test is kept available and is selectively displayed.

2. The method according to claim 1, wherein before the test is carried out, continuously examining previously obtained distance measurements and in an event that the distance measurements fail to reach the lower threshold value for a predetermined period of time:
   a) the specified start signal is emitted, triggering the start of the timekeeping and signaling to the subject that the test is starting; or
   b) the timekeeping is started when the distance measurements exceed a threshold value.

3. The method according to claim 1, wherein an external trigger signal causes an emission of the specified start signal and the start of the timekeeping, or that the timekeeping is started when a sensor placed in a seat surface of the chair detects a drop in pressure below a predetermined threshold value.

4. The method according to claim 1, wherein if the distance measurements fall below the lower threshold value after exceeding another threshold value for a predetermined period of time, the test is terminated and the timekeeping is stopped.

5. The method according to claim 1, wherein an external trigger signal ends the timekeeping, or in that the timekeeping ends when a sensor placed in a seat surface of the chair detects a pressure that exceeds a threshold value.

6. The method according to claim 1, wherein the test is considered incorrect if an increase of the signal exceeds a predetermined increase threshold, and/or if the signal has readings corresponding to the distance of the chair from the wall or the obstacle or has measurements that exceed the distance from the chair to the marking by a predetermined threshold value, and/or if none of the distance measurements of the signal reaches a predetermined threshold value and the subject does not reach a turn-around area, and/or if the timekeeping reaches a maximum time without the test having terminated.

7. The method according to claim 1, wherein the chair is positioned with respect to the wall or the obstacle, in that an orientation of the distance measurement equipment with respect to the wall or the obstacle is continuously monitored, and an error message is output and a measurement result is invalidated if there are changes in the orientation of the distance measurement equipment or deviations in the orientation of the distance measurement equipment by more than a threshold value from a predetermined orientation.

8. The method according to claim 1, wherein prior to carrying out the test, disposing the distance measurement equipment on the backrest of the chair and oriented from the backrest toward a seated subject.

9. The method according to claim 1, which further comprises instructing the subject to get up after an end of the test is terminated and go behind the chair or leave a recording area of the distance measurement equipment, and then a correct position and/or orientation of the chair is checked again according to predetermined criteria, and the test is considered incorrect if the position and/or orientation of the chair to the wall does not meet the predetermined criteria.

10. The method according to claim 1, wherein it is determined whether the distance of the chair or the backrest from the wall or from the obstacle is to great or too small relative to a distance range, and a determination is correspondingly displayed.

11. The method according to claim 1, wherein the distance measurement equipment determines the distance by means of ultrasonic or laser measurement.

12. The method according to claim 1, which further comprises emitting a turn-around signal when the distance measurements of the distance measurement equipment exceed a predetermined distance.

13. The method according to claim 1, wherein the signal is further analyzed in order to determine:
   a) whether the signal remains unchanged within a range of measurement error for individual periods of time; and
   b) whether the signal remains unchanged within the range of measurement error for individual periods of time until the signal falls below a lower threshold value.

14. An apparatus for determining a time required for a Timed Up and Go Test and verifying a result obtained, the apparatus comprising:
   a chair having a seat surface and a backrest;
   a controller connected to said chair;
   distance measurement equipment connected to said controller and connected to said backrest and continuously measuring a distance of an object or subject in front of said chair from said backrest of said chair, and configured to compare the distance measurements obtained before a start of the test with a predetermined threshold value and in this way, determine a correct position of the chair, if the distance measurements obtained are within a predetermined distance range and/or if the orientation of the distance measurement equipment corresponds to a predetermined orientation;

a signal generator disposed downstream of said controller, said signal generator configured to emit a start signal when a trigger signal is present or upon determining that the subject is sitting on said chair;

a timer activated by the start signal;

said controller generating a signal from distance measurements supplied to said controller, and then examining whether the signal:
  a) increases continuously in a first time range, and; and
  b) continuously decreases again after a predetermined turn-around threshold is exceeded, wherein said controller is configured to determine a validity of a test and selectively to display or keep available a time determined by timekeeping when conditions a) and b) are present.

15. The apparatus according to claim 14, wherein said controller is configured so as to continuously examine previously obtained distance measurements before carrying out the test, and in an event that the distance measurements fail to reach a lower threshold value for a predetermined period of time said controller configured to:
  a) emit a start signal for triggering the timekeeping and thus signal to the subject that the test is starting; or
  b) start the timekeeping when the distance measurements exceed a threshold value.

16. The apparatus according to claim 14, wherein:
said controller has a control input for an external trigger signal, and said controller is configured to emit the start signal and start the timekeeping when the external trigger signal is present; or
said chair has a pressure sensor in an area of a seat surface, which is connected to said controller, and said controller is configured to activate the timekeeping if said pressure sensor determines that a pressure has dropped below a predetermined threshold value.

17. The apparatus according to claim 14, wherein said controller is configured so that said controller will end the test and stop the timekeeping if the distance measurements fall below a lower threshold value after exceeding another threshold value for a predetermined period of time.

18. The apparatus according to claim 14, wherein:
said controller has a control input for an external trigger signal, and said controller is configured to terminate the timekeeping if an external trigger signal is present; or
said chair has a pressure sensor in an area of a seat surface which is connected to said controller, and said controller is configured to terminate the timekeeping if said pressure sensor determines that a pressure has risen above a predetermined threshold value.

19. The apparatus according to claim 14, wherein said controller invalidates the test, if an increase of the signal exceeds a predetermined increase threshold, and/or if the signal has readings corresponding to a distance of said chair from the wall or the obstacle or has measurements that exceed the distance from said chair to the marking by a predetermined threshold value, and/or if none of the distance measurements of the signal reaches a predetermined threshold value and the subject does not reach a turn-around area, and/or if the timekeeping reaches a maximum time without the test having terminated.

20. The apparatus according to claim 14, wherein said distance measurement equipment is disposed on said backrest of said chair and is oriented from said backrest toward a seated subject.

21. The apparatus according to claim 14, wherein said distance measurement equipment determines the distance by means of ultrasonic or laser measurement.

* * * * *